(12) United States Patent
Rosenberg et al.

(10) Patent No.: US 10,532,188 B2
(45) Date of Patent: *Jan. 14, 2020

(54) ANCHORING AN INTRAVENOUS CANNULA

(71) Applicant: INTERRAD Medical, Inc., Plymouth, MN (US)

(72) Inventors: Michael S. Rosenberg, Eagan, MN (US); Mark R. Christianson, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 104 days.

This patent is subject to a terminal disclaimer.

(21) Appl. No.: 15/698,074

(22) Filed: Sep. 7, 2017

(65) Prior Publication Data

US 2017/0368312 A1 Dec. 28, 2017

Related U.S. Application Data

(63) Continuation of application No. 14/590,088, filed on Jan. 6, 2015, now Pat. No. 9,782,567, which is a continuation of application No. 13/399,290, filed on Feb. 17, 2012, now Pat. No. 8,932,263.

(51) Int. Cl.
| | |
|---|---|
| *A61M 5/32* | (2006.01) |
| *A61M 31/00* | (2006.01) |
| *A61M 25/04* | (2006.01) |
| *A61M 5/158* | (2006.01) |
| *A61M 25/06* | (2006.01) |
| *A61M 25/02* | (2006.01) |
| *A61B 17/34* | (2006.01) |

(52) U.S. Cl.
CPC ............ *A61M 25/04* (2013.01); *A61M 5/158* (2013.01); *A61B 2017/3484* (2013.01); *A61M 25/0606* (2013.01); *A61M 2005/1586* (2013.01); *A61M 2025/0286* (2013.01)

(58) Field of Classification Search
CPC .. A61B 2017/3484; A61M 2005/1586; A61M 25/04; A61M 25/0606; A61M 5/158; A61M 2025/0286
See application file for complete search history.

(56) References Cited

U.S. PATENT DOCUMENTS

| | | | |
|---|---|---|---|
| 3,039,468 A | 6/1962 | Price | |
| 3,308,819 A | 3/1967 | Arp | |
| 3,765,032 A | 10/1973 | Palma | |
| 3,856,009 A | 12/1974 | Winnie | |
| 3,896,527 A | 7/1975 | Miller et al. | |

(Continued)

FOREIGN PATENT DOCUMENTS

| | | |
|---|---|---|
| EP | 2614851 | 7/2013 |
| WO | WO 1991/15254 | 10/1991 |

(Continued)

OTHER PUBLICATIONS

Johnson & Johnson web page printout, "The EndoANCHOR Comparative Summary" printed Sep. 13, 2005, 2 pages.

(Continued)

*Primary Examiner* — Rebecca E Eisenberg
(74) *Attorney, Agent, or Firm* — Fish & Richardson P.C.

(57) ABSTRACT

Some embodiments of a medical system include a subcutaneous anchor device that extends outwardly from side wall of an intravenous cannula so as to secure the intravenous cannula in a position relative to a skin penetration point.

20 Claims, 9 Drawing Sheets

(56) References Cited

U.S. PATENT DOCUMENTS

| | | |
|---|---|---|
| 3,938,529 A | 2/1976 | Gibbons |
| 4,043,346 A | 8/1977 | Mobley et al. |
| 4,114,618 A | 9/1978 | Vargas |
| 4,164,943 A | 8/1979 | Hill et al. |
| 4,248,224 A | 2/1981 | Jones |
| 4,309,994 A | 1/1982 | Grunwald |
| 4,397,647 A | 8/1983 | Gordon |
| 4,474,569 A | 10/1984 | Newkirk |
| 4,569,344 A | 2/1986 | Palmer |
| 4,592,356 A | 6/1986 | Gutierrez |
| 4,645,492 A | 2/1987 | Weeks |
| 4,665,906 A | 5/1987 | Jervis |
| 4,799,495 A | 1/1989 | Hawkins et al. |
| 4,804,359 A | 2/1989 | Grunwald et al. |
| 4,813,930 A | 3/1989 | Elliott |
| 4,936,823 A | 6/1990 | Colvin et al. |
| 4,986,810 A | 1/1991 | Semrad |
| 5,041,085 A | 8/1991 | Osborne et al. |
| 5,067,957 A | 11/1991 | Jervis |
| 5,122,122 A | 6/1992 | Allgood |
| 5,190,546 A | 3/1993 | Jervis |
| 5,256,146 A | 10/1993 | Ensminger et al. |
| 5,267,960 A | 12/1993 | Hayman et al. |
| 5,279,564 A | 1/1994 | Taylor |
| 5,312,337 A | 5/1994 | Flaherty et al. |
| 5,344,439 A | 9/1994 | Otten |
| 5,368,017 A | 11/1994 | Sorenson et al. |
| 5,378,239 A | 1/1995 | Termin et al. |
| 5,456,671 A | 10/1995 | Bierman |
| 5,496,277 A | 3/1996 | Terrain et al. |
| 5,578,013 A | 11/1996 | Bierman |
| 5,597,378 A | 1/1997 | Jervis |
| 5,599,311 A | 2/1997 | Raulerson |
| 5,653,718 A | 8/1997 | Yoon |
| 5,681,288 A | 10/1997 | Schlitt |
| 5,688,247 A | 11/1997 | Haindl et al. |
| 5,702,371 A | 12/1997 | Bierman |
| 5,707,362 A | 1/1998 | Yoon |
| 5,722,959 A | 3/1998 | Bierman |
| 5,728,133 A | 3/1998 | Kontos |
| 5,741,234 A | 4/1998 | Aboul-Hosn |
| 5,746,720 A | 5/1998 | Stouder, Jr. |
| 5,755,697 A | 5/1998 | Jones et al. |
| 5,769,821 A | 6/1998 | Abrahamson et al. |
| 5,800,402 A | 9/1998 | Bierman |
| 5,810,781 A | 9/1998 | Bierman |
| 5,814,065 A | 9/1998 | Diaz |
| 5,827,230 A | 10/1998 | Bierman |
| 5,833,664 A | 11/1998 | Seare, Jr. |
| 5,833,667 A | 11/1998 | Bierman |
| 5,857,999 A | 1/1999 | Quick et al. |
| 5,921,965 A | 7/1999 | Blei |
| 5,928,266 A | 7/1999 | Kontos |
| 5,944,732 A | 8/1999 | Raulerson et al. |
| 5,947,931 A | 9/1999 | Bierman |
| 5,971,960 A | 10/1999 | Flom et al. |
| 5,984,896 A | 11/1999 | Boyd |
| 5,989,265 A | 11/1999 | Bouquet De La Joliniere et al. |
| 6,213,979 B1 | 4/2001 | Bierman |
| 6,290,676 B1 | 9/2001 | Bierman |
| 6,413,240 B1 | 7/2002 | Bierman et al. |
| 6,447,485 B2 | 9/2002 | Bierman |
| 6,540,693 B2 | 4/2003 | Burbank et al. |
| 6,572,588 B1 | 6/2003 | Bierman et al. |
| 6,582,388 B1 | 6/2003 | Coleman et al. |
| 6,582,403 B1 | 6/2003 | Bierman et al. |
| 6,663,600 B2 | 12/2003 | Bierman et al. |
| 6,679,851 B2 | 1/2004 | Burbank et al. |
| 6,695,861 B1 | 2/2004 | Rosenberg et al. |
| 6,770,055 B2 | 8/2004 | Bierman et al. |
| 6,896,665 B2 | 5/2005 | Picha et al. |
| 6,958,044 B2 | 10/2005 | Burbank et al. |
| 7,056,286 B2 | 6/2006 | Ravenscroft et al. |
| 8,932,263 B2 | 1/2015 | Rosenberg et al. |
| 9,782,567 B2 | 10/2017 | Rosenberg |
| 2002/0068898 A1 | 6/2002 | McGucklin, Jr. et al. |
| 2002/0068899 A1 | 6/2002 | McGucklin, Jr. et al. |
| 2002/0120250 A1 | 8/2002 | Altman |
| 2002/0165489 A1 | 11/2002 | McGucklin, Jr. et al. |
| 2005/0171588 A1 | 8/2005 | Wahlstrom et al. |
| 2005/0187578 A1 | 8/2005 | Rosenberg et al. |
| 2005/0256458 A1 | 11/2005 | Howard et al. |
| 2005/0256459 A1 | 11/2005 | Howard et al. |
| 2006/0079845 A1 | 4/2006 | Howard et al. |
| 2006/0129134 A1 | 6/2006 | Kerr |
| 2007/0021685 A1 | 1/2007 | Oepen et al. |
| 2007/0106330 A1 | 5/2007 | Rosenberg et al. |
| 2007/0225651 A1 | 9/2007 | Rosenberg et al. |
| 2007/0232997 A1 | 10/2007 | Glenn |
| 2008/0275401 A1 | 11/2008 | Sage et al. |
| 2009/0326470 A1 | 12/2009 | Rosenberg et al. |
| 2011/0112508 A1 | 5/2011 | Panzirer |
| 2015/0112309 A1 | 4/2015 | Rosenberg |

FOREIGN PATENT DOCUMENTS

| | | |
|---|---|---|
| WO | WO 2001/021242 | 3/2001 |
| WO | WO 2004/026152 | 4/2004 |
| WO | WO 2005/039419 | 5/2005 |
| WO | WO 2005/102438 | 11/2005 |
| WO | WO 2007/093957 | 8/2007 |
| WO | WO 2010/059714 | 5/2010 |
| WO | WO 2012/007944 | 1/2012 |

OTHER PUBLICATIONS

Johnson & Johnson web page printout, "The EndoANCHOR Features and Benefits" printed Sep. 13, 2005, 2 pages.

Johnson & Johnson web page printout, "The EndoANCHOR Firing Sequences" printed Sep. 13, 2005, 2 pages.

Web Page Printout of Statlock Device, publicly available before Feb. 17, 2012, 1 page.

International Search Report and Written Opinion for Application No. PCT/US2013/026340, dated Jun. 21, 2013, 18 pages.

Implant Manual. "Interstim Therapy: Model 3093 Lead and Model 3889 Lead." Medtronic, Inc., Minneapolis, MN, 2010, 38 pages.

International Preliminary Report on Patentability dated Aug. 28, 2014, 11 pages [no new art].

European Search Report for App. No. 13748481.2, dated Aug. 15, 2015, 13 pages.

European Search Report for App. No. 13748481.2-1405, dated May 27, 2016, 8 pages.

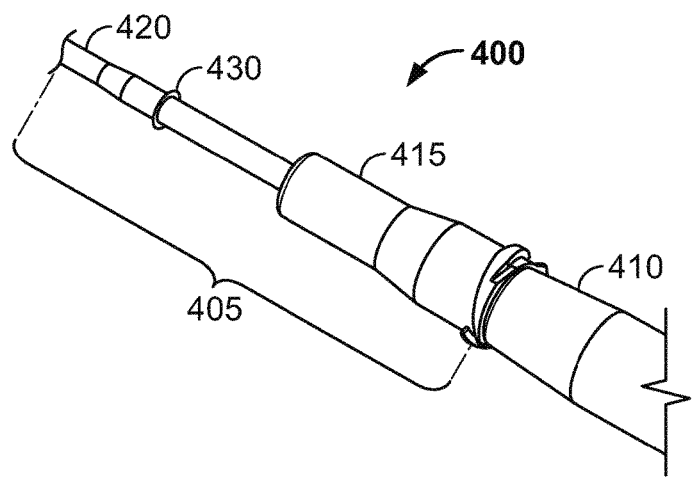 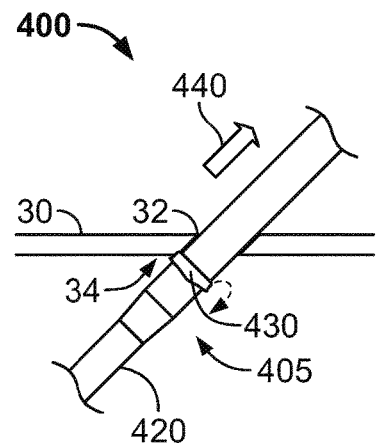
FIG. 4A  FIG. 4B
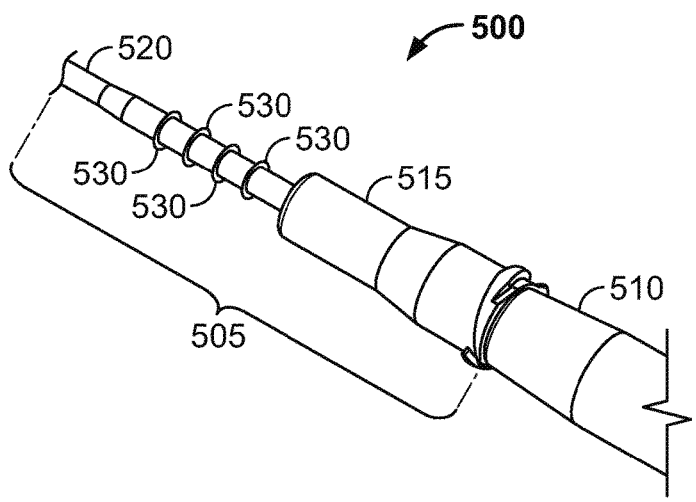 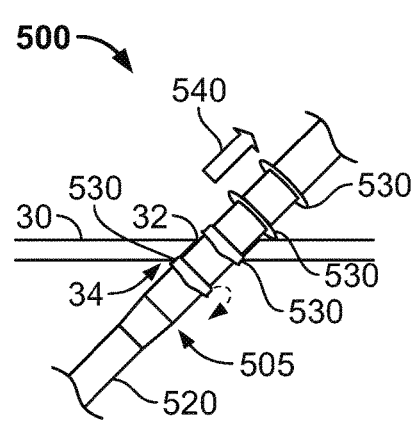
FIG. 5A  FIG. 5B

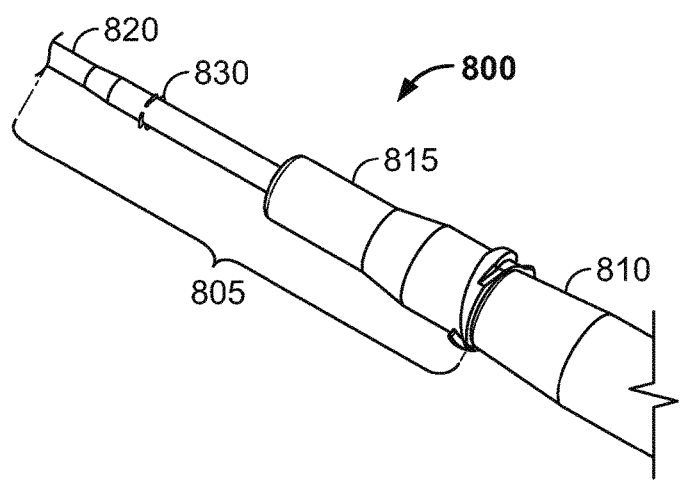
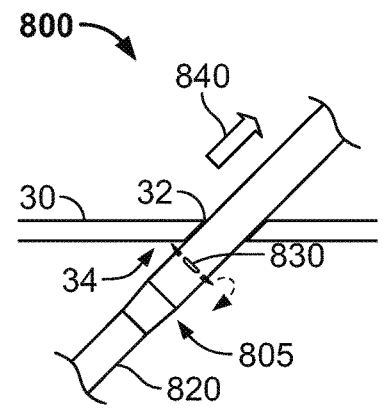
FIG. 8A
FIG. 8B
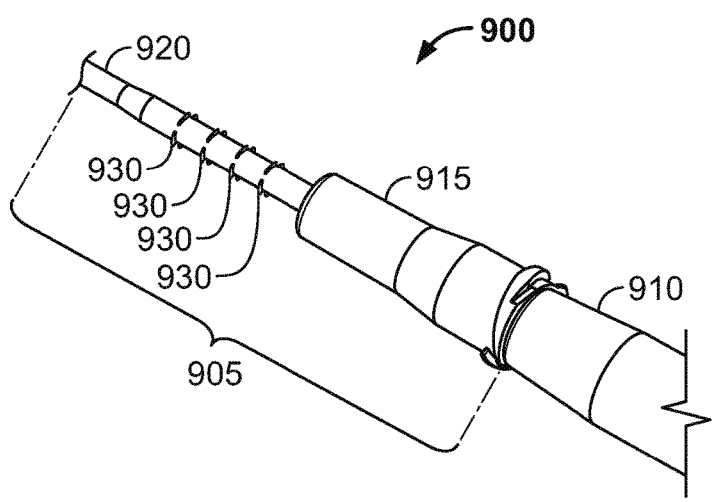
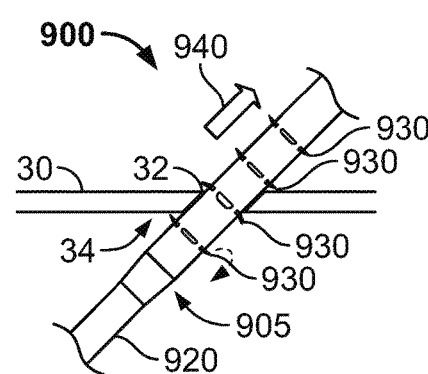
FIG. 9A
FIG. 9B

ANCHORING AN INTRAVENOUS CANNULA

CROSS-REFERENCE TO RELATED APPLICATION(S)

This is a continuation of U.S. patent application Ser. No. 14/590,088 filed Jan. 6, 2015 which is a continuation of U.S. patent application Ser. No. 13/399,290 filed on Feb. 17, 2012, the entire contents of which are incorporated herein by reference.

TECHNICAL FIELD

This document relates to a medical device having an integrated anchor system for securing a portion of the medical device in a subcutaneous region underlying the skin.

BACKGROUND

Some medical devices a configured to provide intravenous therapy in which and an intravenous infusion of a fluid is administered through an intravenous cannula. The intravenous cannula normally includes a distal tip region that is configured to insert through a skin opening and into a selected body vessel (e.g., a vein a patient's arm or leg) while a proximal hub remains external to skin opening for connection with a separate medicinal fluid line. This type of intravenous infusion therapy provides a direct route to the bloodstream which allows for hydration, administration of blood or blood products and administration of medications. Medications that are administered intravenously can achieve therapeutic effects more rapidly and, in some cases, using a lower dose.

Typical intravenous cannulas may extend for several inches in length and normally include a fluid lumen that extends to a distal port and the tip of the cannula. In some version, the intravenous cannula may include large, flat "wings" or "tabs" that remain external to the skin and are equipped to adhere to the outer surface of the patient's skin. In other circumstances, the intravenous cannula may be secured to the skin penetration site using adhesive tape that is wrapped around an outer circumferential surface region of the intravenous cannula and around an adjacent portion of the patient's arm or leg.

SUMMARY

Some embodiments of a medical system include a subcutaneous anchor device that extends outwardly from side wall of an intravenous cannula so as to secure the intravenous cannula in a position relative to a skin penetration point. In some circumstances, the subcutaneous anchor device can be integrally formed as a unitary structure with the side wall of the intravenous cannula so that the subcutaneous anchor device is positioned along a central region of the intravenous cannula (e.g., at a position that is proximal of the distal tip portion configured to penetrate into a targeted vein or other vessel, and that is distal of the proximal connector hub configured to releasably mate with a separate fluid line). As such, the subcutaneous anchors may engage with fatty tissue or other tissue inside the subcutaneous layer immediately underlying the skin near the skin penetration point, thereby providing an anchoring effect without necessarily requiring adhesives applied external to the skin.

Some embodiments described herein include a medical system for anchoring an intravenous cannula device in a subcutaneous region along an underside of a skin layer. The medical system may include an intravenous cannula device and an inserter tool removably coupled to the intravenous cannula device. The intravenous cannula device may include a flexible catheter, a proximal connector hub, and a subcutaneous anchor integrally formed as a unitary structure with an outer wall of the flexible catheter. The flexible catheter may include a lumen and also may extend distally of the proximal connector hub. The proximal connector hub may optionally include a thread pattern configured to releasably connect with an external fluid line. The inserter tool may be removably coupled to the intravenous cannula device so as to insert the flexible catheter of the intravenous cannula device through a skin penetration point and into a targeted vessel. The inserter tool may optionally include a handle and an insertion needle extending distally from the handle. The insertion needle may be slidably engaged with the lumen of the flexible catheter of the intravenous cannula device. The inserter tool may be removable from the intravenous cannula device when the insertion needle is proximally withdrawn from the lumen of the flexible catheter. The subcutaneous anchor of the intravenous cannula device may be positioned between a distal tip of the flexible catheter and the proximal connector hub. The subcutaneous anchor may include at least one surface to engage tissue in a subcutaneous region along an underside of a skin layer when the flexible catheter of the intravenous cannula device is inserted through a skin penetration point and into a targeted vessel.

Particular embodiments include a method of using an intravenous cannula device. The method may include inserting a needle portion of an inserter tool through a skin penetration point and into a targeted vessel. An intravenous cannula device may be removably coupled to the inserter tool such that a flexible catheter of the intravenous cannula device is advanced through the skin penetration point and into the targeted vessel while a subcutaneous anchor integrally formed as a unitary structure with an outer wall of the flexible catheter is positioned in a subcutaneous region along an underside of a skin layer. The method may also include removing the inserter tool from the intravenous cannula device such that the needle portion of the inserter tool is slidably withdrawn from a lumen of the flexible catheter while the flexible catheter remains in the targeted vessel and the subcutaneous anchor remains in the subcutaneous region along the underside of the skin layer. Optionally, the method may include threadably engaging an external fluid line to a proximal connector hub of the intravenous cannula device while the flexible catheter remains in the targeted vessel and the subcutaneous anchor remains in the subcutaneous region along the underside of the skin layer. The subcutaneous anchor may be positioned between a distal tip of the flexible catheter and the proximal connector hub. The subcutaneous anchor may include at least one surface to engage tissue in the subcutaneous region proximate to the skin penetration point.

In other embodiments, a medical system for anchoring an intravenous cannula device in a subcutaneous region along an underside of a skin layer may include an intravenous cannula device. The intravenous cannula device may include a flexible catheter, a proximal connector hub, and a subcutaneous anchor positioned between a distal tip of the flexible catheter and the proximal connector hub. The system may also include an inserter tool removably coupled to the intravenous cannula device. The inserter tool may optionally include a handle and an insertion needle extending distally from the handle. The insertion needle may be slidably engaged with a lumen of the flexible catheter. The subcutaneous anchor may include at least one surface to engage tissue in a subcutaneous region along an underside of a skin layer when the flexible catheter of the intravenous cannula device is into a targeted vessel.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A and 4B are perspective and side views of an intravenous cannula system having a subcutaneous anchor including a circumferential ring, in accordance with some alternative embodiments.

FIGS. 5A and 5B are perspective and side views of an intravenous cannula system having subcutaneous anchors including a multiple circumferential ring, in accordance with some alternative embodiments.

FIGS. 8A and 8B are perspective and side views of an intravenous cannula system having a subcutaneous anchor including a slotted circumferential ring, in accordance with some alternative embodiments.

FIGS. 9A and 9B are perspective and side views of an intravenous cannula system having subcutaneous anchors including multiple slotted circumferential rings, in accordance with some alternative embodiments.

Like reference symbols in the various drawings indicate like elements.

DETAILED DESCRIPTION OF ILLUSTRATIVE EMBODIMENTS

Figure 1:
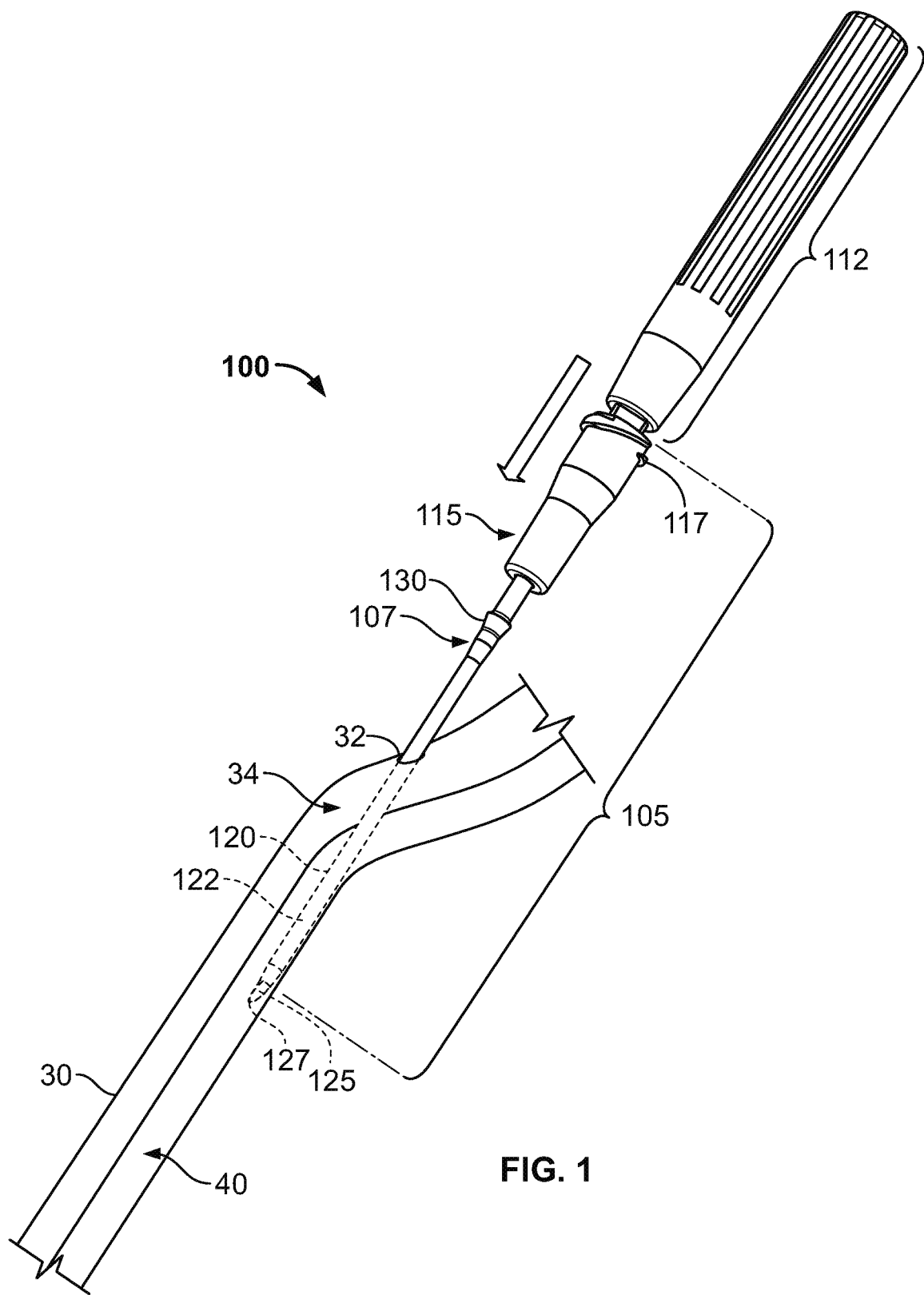
FIGS. 1-3 are perspective views of an intravenous cannula system having a subcutaneous anchor, in accordance with some embodiments.
Figure 2:
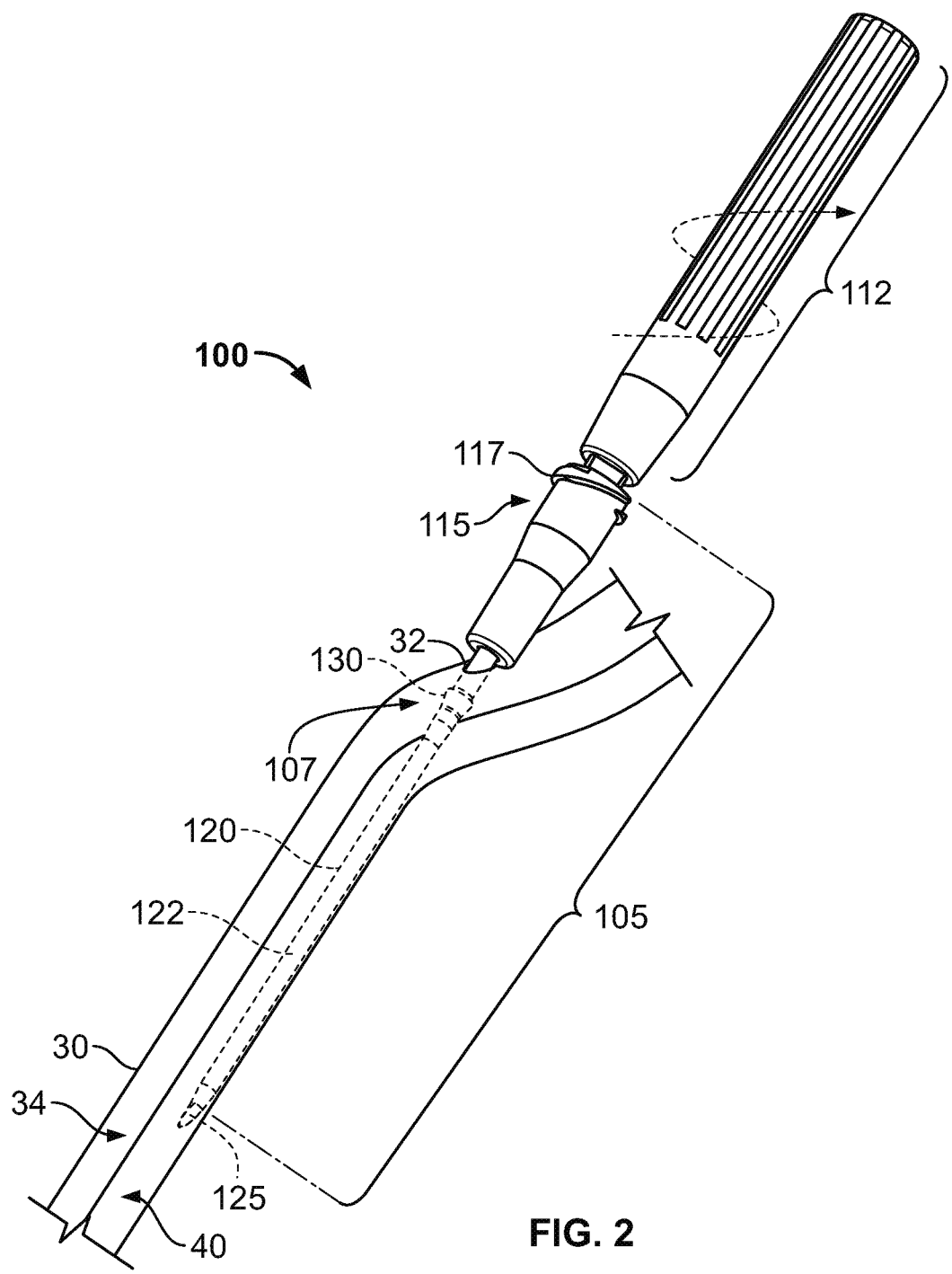
Figure 3:
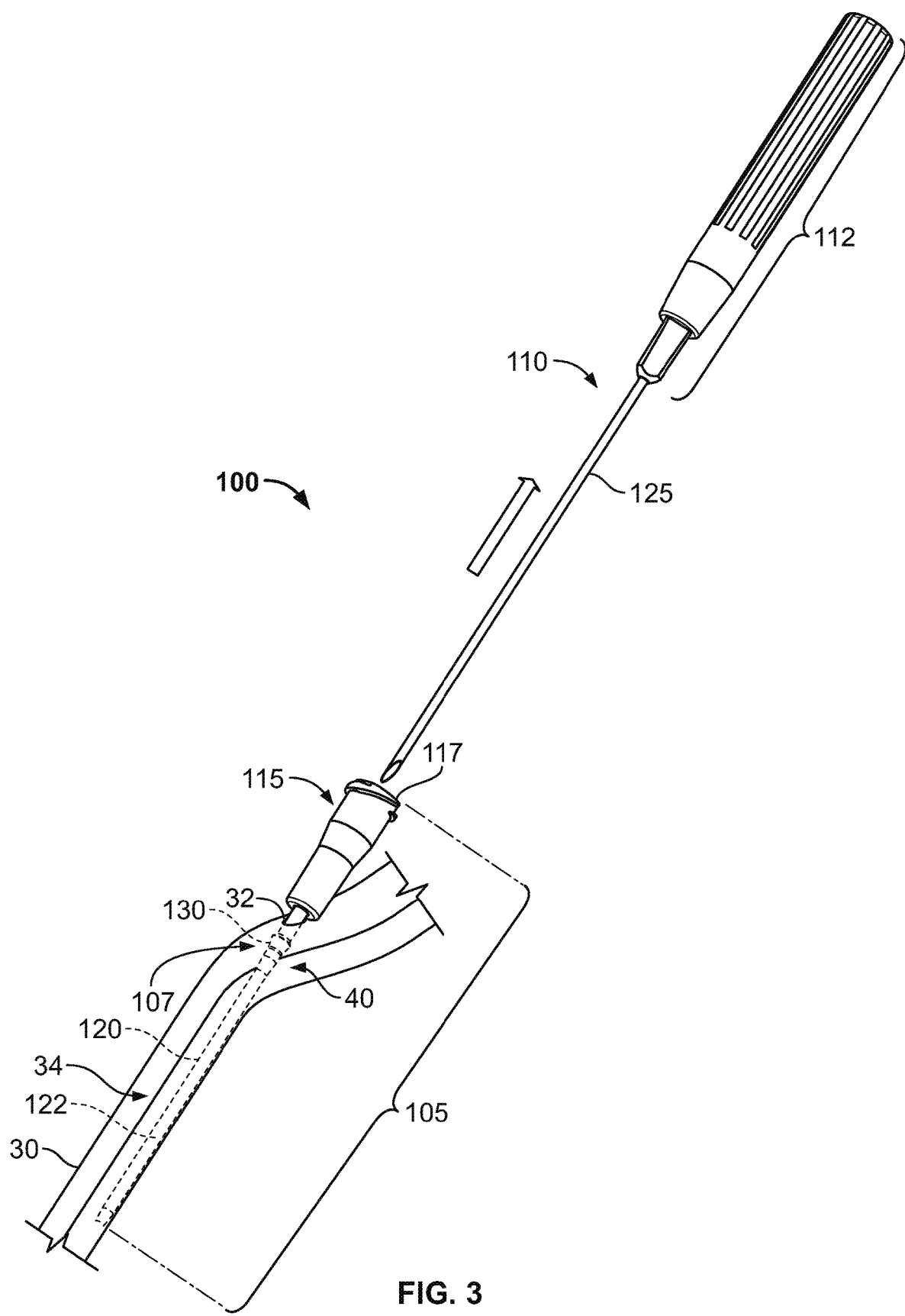

Referring to FIGS. 1-3, a medical system 100 includes an intravenous cannula device 105 that is equipped with a subcutaneous anchor 130 so as to secure the intravenous cannula device 105 in a position relative to a skin penetration point 32. In this embodiment, the subcutaneous anchor 130 can be integrally formed as a unitary structure with the side wall of the intravenous cannula device 105. The intravenous cannula device 105 can include a distal section having a flexible catheter 120 and a proximal connector hub 115 configured to releasably connect with an external fluid line (not shown in FIGS. 1-3). As described in more detail below, the subcutaneous anchor 130 can be positioned along a central region of the intravenous cannula 105 such that the anchor 130 is arranged proximal to a distal tip 122 of the catheter 120 and is arranged distal to the proximal connector hub 115. In particular embodiments, the subcutaneous anchor 130 is located in the central region 107 and extends radially outward of a cylindrical wall the catheter 120 so that the subcutaneous anchor 130 may engage with fatty tissue or other tissue inside the subcutaneous layer 34 immediately underlying the skin 30 near the skin penetration point 32, thereby providing an anchoring effect without necessarily requiring adhesives applied external to the skin 30.

The system 100 depicted in FIGS. 1-3 also includes an inserter tool 110 (FIG. 3) that is detachably connected to the intravenous cannula device 105. In this embodiment, the inserter tool 110 includes a handle 112 configured to be grasped by a user in order to control the insertion of the intravenous cannula device 105 through the skin penetration point 32. As described in more detail below, the inserted tool 110 is removably coupled to the intravenous cannula device 105 so that an insertion needle 125 of the inserter tool 110 provides support to the flexible catheter 120 during insertion of the distal tip 122 of the flexible catheter 120 into a targeted body vessel 40. After the inserter tool 110 is used to facilitate placement of the intravenous cannula device 105, the inserter tool 110 can be removed from the intravenous cannula device 105 while the distal tip 122 of the flexible catheter 120 remains in the targeted body vessel 40, thereby providing a fluid communication line between the proximal connector hub 115 and the targeted body vessel 40 via the flexible catheter 120.

Still referring to FIGS. 1-3, the proximal connector hub 115 of the intravenous cannula device 105 includes a fluid fitting 117 that is configured to releasably mate with an external fluid line. For example, the fluid fitting 117 may provide a luer connector, which includes a threaded region and a sealing face at the proximal-most end region of the proximal connector hub 115, for purposes of detachably coupling to an external fluid line (e.g., a supply of intravenous fluid, a medicine delivery line, a blood infusion line, a blood withdrawal line, or the like). The proximal connector hub 115 includes a generally rigid body having an outer radius that is substantially larger than the outer radius of the flexible catheter 120. In this embodiment, the outer radius of the proximal connector hub 115 is also larger than the skin penetration point 32 such that the proximal connector hub 115 remains external to the skin 30 during use. The proximal connector hub 115 includes a central lumen that is in fluid communication with a corresponding lumen of the flexible catheter 120. Accordingly, in the embodiment depicted in FIGS. 1-3, the catheter 120 can be inserted into through the penetration point 32, to the underside of the skin 30, and into a vein 40 or other targeted vessel to provide vascular access for intravenous infusion or withdrawal of a fluid.

In some embodiments, the catheter 120 may be flexible. For example, the catheter 120 can be configured to flexibly contour with the curvatures of the targeted vessel 40. As previously described, the catheter 120 can be supported by the insertion needle 125 on the inserter tool 110 during the initial placement of the flexible catheter 120 into the targeted vessel 40. In such embodiments, the insertion needle 125 removably occupies the lumen of the catheter 120, and provides support for the catheter 120 against bending or bucking during insertion into the targeted vessel 40. In some implementations, the insertion needle 125 is equipped with a sharp tip 127 that protrudes from the distal tip of the catheter 120 (refer to FIGS. 1-2) such that the inserter tool 110 provides the initial penetration path through the skin 32 and into the targeted vessel 40.

The catheter 120 can be configured to have an axial length which is substantially greater than the axial length of the proximal connector hub 115. For example, in some embodiments, the axial length of the catheter 20 (extending from the junction with the proximal connector hub 115 to the distal-most end of the catheter tip) can be about 25 mm to about 150 mm, about 40 mm to about 70 mm, and preferably about 50 mm. The catheter may also include an outer diameter of about 12-gauge to about 28-gauge, and preferable about 14-gauge to about 24-gauge sizes. Such an axial length and diameter size can be advantageous for providing access to the targeted vessel 40 while not necessary requiring advancement deep into the vasculature. Also, the overall axial length of the intravenous cannula device 105 (extending from the proximal end of the proximal connector hub 115 to the distal-most end of the catheter tip) can be about 45 mm to about 170 mm, about 60 mm to about 90 mm, and preferably about 70 mm. Such an axial length can be advantageous for providing access to the targeted vessel while also maintaining the proximal connector hub 115 at a location external to the skin and near the skin penetration point 32.

Still referring to FIGS. 1-3, the flexible catheter 120 can extend distally from the proximal connector hub 115, and the proximal portion of the flexible catheter can define the central region 107 of the intravenous cannula device 105 at which the subcutaneous anchor 130 is located. In this embodiment, the subcutaneous anchor 130 is formed about the periphery of the catheter 120 at a position that is substantially closer to the proximal connector hub 115 than to the distal tip 122 of the catheter 120. The subcutaneous anchor 130 is positioned to reside in the subcutaneous layer 34 along the underside of the skin 30 and near the skin penetration point 32. Accordingly, while the catheter 120 can penetrate into the targeted vessel 40, the subcutaneous anchor 130 is positioned along to the intravenous cannula device 105 to reside external to the vessel 40 but under the skin 30 in the subcutaneous layer 34. Furthermore, while the subcutaneous anchor 130 is positioned in the subcutaneous layer 34, the proximal connector hub 115 remains external to the skin 30 so as to receive a connection with an external fluid line.

As described in more detail below, the subcutaneous anchor 130 can be directed to penetrate through the same penetration point 32 as the catheter 120 to maintain a position of the subcutaneous anchor 130 in the subcutaneous layer 34 along the underside of the skin 30. As such, the subcutaneous anchor 130 can secure the catheter 120 in the operative position relative to the penetration point 32 without necessarily requiring adhesives bonded to the skin. In some embodiments, the subcutaneous anchor 130 can be integrally formed with the catheter 120 as a unitary such that the subcutaneous anchor 130 and the catheter 120 share a common material. The subcutaneous anchor 130 can include one or more structures that extend outwardly from outer circumference of the catheter 120. For example, the subcutaneous anchor 130 can include one or more rings, flexible flaps, spirals, flexible tabs, tines, barbs, or the like that, after insertion, are deployed in the subcutaneous region 34 so as to secure the position of the intravenous cannula device 105 relative to the skin penetration point 32. Various examples of the subcutaneous anchor 130 are described below in connection with FIGS. 4-16.

In use, the system 100 can be manipulated by a user so as to deliver the distal tip of intravenous cannula device 105 into the targeted vessel 40, and then the system 100 can be adjusted to provide a fluid communication line to the targeted vessel 40. For example, as shown in FIG. 1, the handle 112 of the inserter tool 110 can be grasped by the user so as to forcibly advance the sharp tip 127 of the insertion needle 125 through the skin 30 and into the targeted vessel 40. In doing so, the flexible catheter 120 of the intravenous cannula device 105 (which is slidably received on the insertion needle 125) is also advanced through the penetration point 32 and into the targeted vessel 40.

As shown in FIG. 2, the system 100 can be further advanced after the skin penetration point 32 is formed so that the subcutaneous anchor 130 is likewise advanced through the skin penetration point 32. In such circumstances, the subcutaneous anchor 130 is positioned external to the vessel 40 but under the skin 30 in the subcutaneous layer 34. The subcutaneous anchor 130 includes one or more structures that are configured to engage the underside of the skin 30, the fatty tissues in the subcutaneous layer 34, or both so as to resist withdrawal of the intravenous cannula device 105 from the skin penetration point 32. Thus, the intravenous cannula device 105 is anchored in the operative position relative to the penetration point 32 so that the distal tip of the flexible catheter 120 resides in the targeted vessel 40 while the proximal connector hub 115 resides external to the skin 30. Preferably, the proximal connector hub 115 comprises a substantially transparent polymer material so that the user can directly visualize blood return filling into an internal chamber at the hub when the distal end of the catheter 120 is positioned within the vessel 40.

After the intravenous cannula device 105 is anchored in the operative position, the inserter tool 110 of the system can be released from the intravenous cannula device 105. For example, the inserter tool 110 can be frictionally or threadably engaged with the intravenous cannula device 105. If the inserter tool 110 is engaged with the intravenous cannula device 105 by a friction fit, the user can apply a withdrawal force to the handle 112 of the inserter tool 110 relative to the intravenous cannula device 105. If the inserter tool is threadably engaged with the intravenous cannula device 105, the user can applied a rotational motion to the handle 112 of the inserter tool 110 relative to the intravenous cannula device 105 so as to decouple to the two components. In the illustrated example in FIG. 2, the inserter tool 110 can be released from the intravenous cannula device 105 by twisting (e.g., unscrewing) the handle 112 relative to the intravenous cannula device 105.

As shown in FIG. 3, after the intravenous cannula device 105 is anchored in the operative position, the inserter tool 110 can be fully removed from the intravenous cannula device 105. In the illustrated example, the needle 125, which had occupied the interior space of the catheter 120 in FIGS. 1 and 2, has been longitudinally withdrawn from the catheter 120 through the proximal connector hub 115. As such, the needle 125 no longer reinforces the flexible catheter 120, and allows the catheter 120 to flexibly comply with curvatures of the vein 40 (e.g., in the event of patient movement). Furthermore, the central lumen of the catheter 120 is then free to provide fluid communication between the proximal connector portion 115 and the targeted vessel 40. Accordingly, the proximal connector hub 115 can be mated with an external fluid line, such as an IV drip line or a medicine infusion line.

In some alternative embodiments, the inserter tool 110 can be equipped with a retractable needle (rather than the fixed needle 125 that can receive a safety cap after removal). The retractable needle of the inserter tool may be retractable relative to the handle 112, which can improve user safety and reduce the likelihood of inadvertent needle wounds. For example, the retractable needle may have a length that is similar to the needle 124 depicted in FIG. 3, but the retractable needle can be spring-loaded to ejected proximally away from the lumen of the flexible catheter and into an internal receiving chamber defined inside the handle 112 when the inserter tool is withdrawn from the intravenous cannula device 105. In such circumstances, the handle may have a greater length than the embodiment depicted in FIG. 3 so as to fully receive the retracted needle). Alternatively or additionally, the inserter tool can be equipped with a protective cap piece that is movable to cover the tip of the needle (either the fixed needle 125 or the spring-biased retractable needle) when the inserter tool is withdrawn from the intravenous cannula device 105.

In the embodiment depicted in FIGS. 1-3, the subcutaneous anchor 130 is integrally formed with the outer wall of the flexible catheter 120. The shape of the anchor device 130 can be selected to provide improved anchoring or withdrawal benefits depending upon the configuration of the catheter 120 and the selected location of the skin penetration point along a patient's body. For example, as shown in FIGS. 1-3, the subcutaneous anchor 130 can include a tapered ring structure that extends around the circumference of the catheter 120 and provides a substantially greater outer diameter size than the generally cylindrical body portion of the catheter 120. The tapered ring structure can have a tapered wall that extends toward the distal tip 122 of the catheter 120 so as to facilitate insertion through the skin penetration point 32, while a proximal-facing ridge of the subcutaneous anchor device 130 resists withdrawal of the intravenous cannula device 105 while the subcutaneous anchor device 130 resides in the subcutaneous layer 34. In some alternative embodiments, the subcutaneous anchor device 130 can be provided in different forms along the central region 107 of the intravenous cannula device 105.

Referring now to FIGS. 4A-4B, some alternative embodiments of a medical system 400 may include a subcutaneous anchor 430 having a different configuration, for example, in the shape of a flexible circumferential ring. In this embodiment, the medical system 400 can be similar to the medical system 100 of FIGS. 1-3. For example, the medical system 400 includes an intravenous cannula device 405 and an inserter tool 410 that is detachably coupled to the intravenous cannula device 405. The intravenous cannula device 405 can include a distal section having a flexible catheter 420 and a proximal connector hub 415 configured to releasably connect with an external fluid line (not shown in FIGS. 4A-4B). In this embodiment, the flexible circumferential ring 430 is integrally formed as a unitary structure with the side wall of the flexible catheter 420, and the flexible circumferential ring 430 is positioned along a central region of the intravenous cannula device 405 (e.g., proximal to a distal tip of the catheter 420 and distal to the proximal connector hub 415).

The flexible circumferential ring 430 is formed radially about the catheter 420 at a location near to the proximal connector hub 415. The flexible circumferential ring 430 can be directed to penetrate through the same penetration point 32 as the catheter 420 for positioning in the subcutaneous layer 34 along the underside of the skin 30. As such, the flexible circumferential ring 430 can secure the catheter 420 in the operative position relative to the penetration point 32 without necessarily requiring adhesive tapes bonded to the skin. In some embodiments, the flexible circumferential ring 430 can be integrally formed with the flexible catheter 420 such that the flexible circumferential ring 430 and the catheter 420 share a common flexible polymer material. Accordingly, during insertion through the skin penetration point, the flexible circumferential ring 430 can flexibly adjust in a first direction so that the outer rim of the flexible circumferential ring 430 is shifted toward the circumferential wall of the catheter 420 (in a proximal direction toward the proximal connector hub 415). After insertion of the flexible circumferential ring 430 through the skin penetration point and into the subcutaneous layer 34, the flexible circumferential ring 430 can be biased to extend outwardly from the circumferential wall of the catheter 420. In doing so, the flexible circumferential ring 430 can operate as a subcutaneous anchor that engages the underside of the skin 30, the fatty tissues in the subcutaneous layer 34, or both so as to resist withdrawal of the intravenous cannula device 405 from the skin penetration point 32. Thus, the intravenous cannula device 405 can be anchored in the operative position relative to the penetration point 32 so that the distal tip of the flexible catheter 420 resides in the targeted vessel 40 while the proximal connector hub 415 resides external to the skin 30.

Referring to FIG. 4B, during removal of the intravenous cannula device 405, the flexible circumferential ring 430 can flexibly adjust in a second direction so that the outer rim of the flexible circumferential ring 430 is shifted toward the circumferential wall of the catheter 420 (in a distal direction away the proximal connector hub 415). Thus, the flexible circumferential ring 430 can be configured to prolapse in response to a removal force 440 applied to the intravenous cannula device 405 during withdrawal of the intravenous cannula device 405 from the skin penetration point.

Referring now to FIGS. 5A-5B, some alternative embodiments of a medical system 500 may include an intravenous cannula device 505 that is similar to the device 405 illustrated in FIGS. 4A-4B, except that intravenous cannula device 505 is equipped with multiple subcutaneous anchors 530 in the shape of flexible circumferential rings. Similar to previously described embodiments herein, the medical system 500 includes the intravenous cannula device 505 and an inserter tool 510 that is detachably coupled to the intravenous cannula device 505. The intravenous cannula device 505 can include a distal section having a flexible catheter 520 and a proximal connector hub 515 configured to releasably connect with an external fluid line. In this embodiment, each of the flexible circumferential rings 530 is integrally formed as a unitary structure with the side wall of the flexible catheter 520, and the flexible circumferential rings 530 are positioned in series along a central region of the intravenous cannula device 505 (e.g., proximal to a distal tip of the catheter 520 and distal to the proximal connector hub 515).

Similar to the embodiments previously described in connection with FIGS. 4A-4B, one or more of the flexible circumferential rings 530 can be directed to penetrate through the same penetration point 32 as the catheter 520 for positioning in the subcutaneous layer 34 along the underside of the skin 30. As such, one or more of the flexible circumferential rings 530 can secure the catheter 520 in the operative position relative to the penetration point 32 without necessarily requiring adhesive tapes bonded to the skin. Each of the flexible circumferential rings 530 inserted through the skin penetration point 32 can flexibly adjust in a first direction so that the outer rim of the respective circumferential ring 530 is shifted toward the circumferential wall of the catheter 520 (in a proximal direction toward the proximal connector hub 515). After insertion of the respective circumferential ring 530 through the skin penetration point 32 and into the subcutaneous layer 34, the respective circumferential ring 530 can be biased to extend outwardly from the circumferential wall of the catheter 520. In doing so, the respective circumferential ring 530 can operate as a subcutaneous anchor that engages the underside of the skin 30, the fatty tissues in the subcutaneous layer 34, or both so as to resist withdrawal of the intravenous cannula device 505 from the skin penetration point 32. Thus, the intravenous cannula device 505 can be anchored in the operative position relative to the penetration point 32 so that the distal tip of the flexible catheter 520 resides in the targeted vessel 40 while the proximal connector hub 515 resides external to the skin 30.

Referring to FIG. 5B, during removal of the intravenous cannula device 505, each of the flexible circumferential rings 530 passing through the skin penetration point 32 can flexibly adjust in a second direction so that the outer rim of the respective circumferential ring 530 is shifted toward the circumferential wall of the catheter 520 (in a distal direction away the proximal connector hub 515). Thus, the respective circumferential ring 530 withdrawing through the skin penetration point 32 can be configured to prolapse in response to a removal force 540 applied to the intravenous cannula device 505 during withdrawal of the intravenous cannula device 505 from the skin penetration point. Any of the flexible circumferential rings 530 that are withdrawn through the skin penetration point 32 or are otherwise positioned external to the skin 30 can return to its non-prolapsed condition in which the flexible circumferential ring 530 is biased to extend generally radially outward from the circumferential wall of the catheter 520.

Figure 6A:
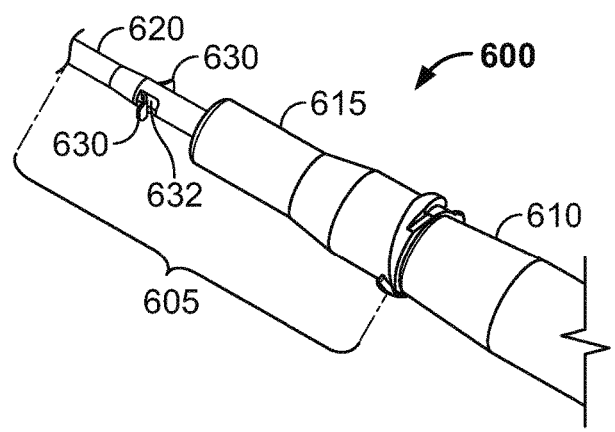
FIGS. 6A and 6B are perspective and side views of an intravenous cannula system having subcutaneous anchors including a pair of recessed tabs, in accordance with some alternative embodiments.
Figure 6B:
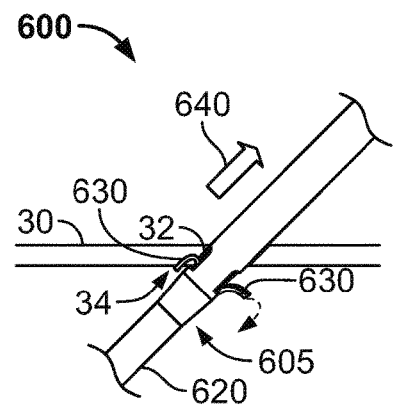

Referring now to FIGS. 6A-6B, some alternative embodiments of a medical system 600 may include a subcutaneous anchor 630 having a different configuration, for example, in the shape of a pair of recessed tabs. In this embodiment, the medical system 600 can be similar to the medical system 100 of FIGS. 1-3. For example, the medical system 600 includes an intravenous cannula device 605 and an inserter tool 610 that is detachably coupled to the intravenous cannula device 605. The intravenous cannula device 605 can include a distal section having a flexible catheter 620 and a proximal connector hub 615 configured to releasably connect with an external fluid line. In this embodiment, each of the recessed tabs 630 are integrally formed as a unitary structure with the side wall of the flexible catheter 620, and the recessed tabs 630 are positioned along a central region of the intravenous cannula device 605 (e.g., proximal to a distal tip of the catheter 620 and distal to the proximal connector hub 615).

Each recessed tab 630 can include a corresponding cavity 632 that is shaped to receive the respective recessed tab 630 during insertion through the skin penetration point 32. Also, the pair of recessed tabs 630 can be arranged diametrically opposite from one another about the central axis of the catheter 620 at a location near to the proximal connector hub 615. In this embodiment, each of the recessed tabs 630 includes a curved shape in which a concave major surface faces generally toward the distal end of the catheter 620 while a convex minor surface faces generally toward the proximal connector hub 615. The pair of recessed tabs 630 can be directed to penetrate through the same penetration point 32 as the catheter 620 for positioning in the subcutaneous layer 34 along the underside of the skin 30. As such, the pair of recessed tabs 630 can secure the catheter 620 in the operative position relative to the penetration point 32 without necessarily requiring adhesive tapes bonded to the skin.

In some embodiments, the pair of recessed tabs 630 can be integrally formed with the flexible catheter 620 such that the pair of recessed tabs 630 and the catheter 420 share a common flexible polymer material. Accordingly, during insertion through the skin penetration point, each of the recessed tabs 630 can flexibly adjust in a first direction (toward the proximal connector hub 615) so that each tab 630 nests within its corresponding cavity 632. After insertion of the recessed tabs 630 through the skin penetration point 32 and into the subcutaneous layer 34, the recessed tabs 630 can be biased to extend outwardly from the circumferential wall of the catheter 620. In doing so, the pair of recessed tabs 630 can operate as subcutaneous anchors that engage the underside of the skin 30, the fatty tissues in the subcutaneous layer 34, or both so as to resist withdrawal of the intravenous cannula device 605 from the skin penetration point 32. Thus, the intravenous cannula device 605 can be anchored in the operative position relative to the penetration point 32 so that the distal tip of the flexible catheter 620 resides in the targeted vessel 40 while the proximal connector hub 615 resides external to the skin 30.

Referring to FIG. 6B, during removal of the intravenous cannula device 605, each of the recessed tabs 630 can flexibly adjust in a second direction to bend or prolapse (in a distal direction away the proximal connector hub 615). Thus, the recessed tabs 630 can be configured to prolapse in response to a removal force 640 applied to the intravenous cannula device 605 during withdrawal of the intravenous cannula device 605 from the skin penetration point. Optionally, each of the recessed tabs 630 can include a second cavity (not shown) positioned distal of the respective tab 630 so as to receive at least a portion of the tab 630 during removal through the skin penetration point 32.

Figure 7A:
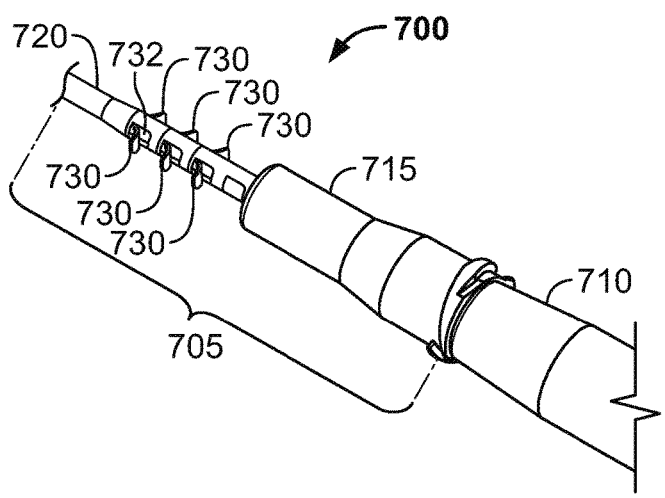
FIGS. 7A and 7B are perspective and side views of an intravenous cannula system having subcutaneous anchors including multiple pairs of recessed tabs, in accordance with some alternative embodiments.
Figure 7B:
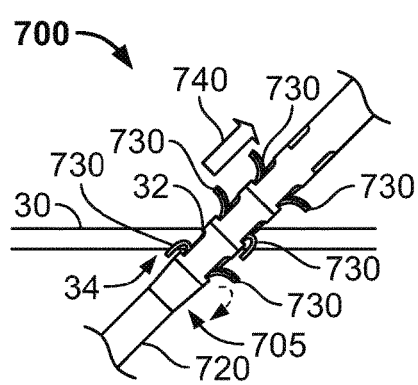

Referring now to FIGS. 7A-7B, some alternative embodiments of a medical system 700 may include an intravenous cannula device 705 that is similar to the device 605 illustrated in FIGS. 6A-6B, except that intravenous cannula device 705 is equipped with multiple pairs of recessed tabs 730 that are operable to provide subcutaneous anchoring. Similar to previously described embodiments herein, the medical system 700 includes the intravenous cannula device 705 and an inserter tool 710 that is detachably coupled to the intravenous cannula device 705. The intravenous cannula device 705 can include a distal section having a flexible catheter 720 and a proximal connector hub 715 configured to releasably connect with an external fluid line. In this embodiment, each of the recessed tabs 730 is integrally formed as a unitary structure with the side wall of the flexible catheter 720, and the pairs of recessed tabs 730 are positioned in series along a central region of the intravenous cannula device 705 (e.g., proximal to a distal tip of the catheter 720 and distal to the proximal connector hub 715).

Similar to the embodiments previously described in connection with FIGS. 6A-6B, one or more of the pairs of recessed tabs 730 can be directed to penetrate through the same penetration point 32 as the catheter 720 for positioning in the subcutaneous layer 34 along the underside of the skin 30. As such, one or more of the pairs of recessed tabs 730 can secure the catheter 720 in the operative position relative to the penetration point 32 without necessarily requiring adhesive tapes bonded to the skin. Each of the recessed tabs 730 inserted through the skin penetration point 32 can flexibly adjust in a first direction (toward the proximal connector hub 715) so that each tab 730 nests within its corresponding cavity 732. After insertion of the respective pair of recessed tabs 730 through the skin penetration point 32 and into the subcutaneous layer 34, the respective pair of recessed tabs 730 can be biased to extend outwardly from the circumferential wall of the catheter 720 (similar to the previous embodiments described in connection with FIGS. 6A-6B). In doing so, the respective pair of recessed tabs 730 can operate as subcutaneous anchors that engage the underside of the skin 30, the fatty tissues in the subcutaneous layer 34, or both so as to resist withdrawal of the intravenous cannula device 705 from the skin penetration point 32. Thus, the intravenous cannula device 705 can be anchored in the operative position relative to the penetration point 32 so that the distal tip of the flexible catheter 720 resides in the targeted vessel 40 while the proximal connector hub 715 resides external to the skin 30.

Referring to FIG. 7B, during removal of the intravenous cannula device 705, each of the pairs of recessed tabs 730 passing through the skin penetration point 32 can flexibly adjust in a second direction to bend or prolapse (in a distal direction away the proximal connector hub 715). Thus, the respective pair of recessed tabs 730 (when withdrawing through the skin penetration point 32) can be configured to prolapse in response to a removal force 740 applied to the intravenous cannula device 705 during withdrawal of the intravenous cannula device 705 from the skin penetration point 32. Any of the recessed tabs 730 that are withdrawn through the skin penetration point 32 or are otherwise positioned external to the skin 30 can return to their non-prolapsed condition in which the recessed tabs 730 are biased to extend generally outward from the respective cavities 732. Optionally, each of the recessed tabs 730 can include a second cavity (not shown) positioned distal of the respective tab 730 so as to receive at least a portion of the tab 730 during removal through the skin penetration point 32.

Referring now to FIGS. 8A-8B, some alternative embodiments of a medical system 800 may include a subcutaneous anchor 830 having a different configuration, for example, in the shape of a slotted circumferential ring. In this embodiment, the medical system 800 can be similar to the medical system 100 of FIGS. 1-3. For example, the medical system 800 includes an intravenous cannula device 805 and an inserter tool 810 that is detachably coupled to the intravenous cannula device 805. The intravenous cannula device 805 can include a distal section having a flexible catheter 820 and a proximal connector hub 815 configured to releasably connect with an external fluid line. In this embodiment, the slotted circumferential ring 830 is integrally formed as a unitary structure with the side wall of the flexible catheter 820, and the slotted circumferential ring 830 is positioned along a central region of the intravenous cannula device 805 (e.g., proximal to a distal tip of the catheter 820 and distal to the proximal connector hub 815).

The slotted circumferential ring 830 is formed radially about the catheter 820 at a location near to the proximal connector hub 815. The slotted circumferential ring 830 can be directed to penetrate through the same penetration point 32 as the catheter 820 for positioning in the subcutaneous layer 34 along the underside of the skin 30. Accordingly, the slotted circumferential ring 830 can secure the catheter 820 in the operative position relative to the penetration point 32 without necessarily requiring adhesive tapes bonded to the skin. In some embodiments, the slotted circumferential ring 830 can be integrally formed with the flexible catheter 820 such that the slotted circumferential ring 830 and the catheter 820 share a common flexible polymer material. Accordingly, during insertion through the skin penetration point, the slotted circumferential ring 830 can flexibly adjust in a first direction so that the outer edge segments of the slotted circumferential ring 830 are shifted toward the circumferential wall of the catheter 820 (in a proximal direction toward the proximal connector hub 815). After insertion of the slotted circumferential ring 830 through the skin penetration point 32 and into the subcutaneous layer 34, the slotted circumferential ring 830 can be biased so that the outer edge segments extend generally radially outward from the circumferential wall of the catheter 830. In doing so, the slotted circumferential ring 830 can operate as a subcutaneous anchor that engages the underside of the skin 30, the fatty tissues in the subcutaneous layer 34, or both so as to resist withdrawal of the intravenous cannula device 805 from the skin penetration point 32. The intravenous cannula device 805 can be anchored in the operative position relative to the penetration point 32 so that the distal tip of the flexible catheter 820 resides in the targeted vessel 40 while the proximal connector hub 815 resides external to the skin 30.

Referring to FIG. 8B, during removal of the intravenous cannula device 805, the slotted circumferential ring 830 can flexibly adjust in a second direction so that the outer edge segments of the slotted circumferential ring 830 are shifted toward the circumferential wall of the catheter 820 (in a distal direction away the proximal connector hub 815). As such, the flexible circumferential ring 830 can be configured to prolapse in response to a removal force 840 applied to the intravenous cannula device 805 during withdrawal of the intravenous cannula device 805 from the skin penetration point 32.

Referring now to FIGS. 9A-9B, some alternative embodiments of a medical system 900 may include an intravenous cannula device 905 that is similar to the device 805 illustrated in FIGS. 8A-8B, except that intravenous cannula device 905 is equipped with multiple subcutaneous anchors 930 in the shape of slotted circumferential rings. Similar to previously described embodiments herein, the medical system 900 includes the intravenous cannula device 905 and an inserter tool 910 that is detachably coupled to the intravenous cannula device 905. The intravenous cannula device 905 can include a distal section having a flexible catheter 920 and a proximal connector hub 915 configured to releasably connect with an external fluid line. In this embodiment, each of the slotted circumferential rings 930 is integrally formed as a unitary structure with the side wall of the flexible catheter 920, and the slotted circumferential rings 930 are positioned in series along a central region of the intravenous cannula device 905 (e.g., proximal to a distal tip of the catheter 920 and distal to the proximal connector hub 915).

Similar to the embodiments previously described in connection with FIGS. 8A-8B, one or more of the slotted circumferential rings 930 can be directed to penetrate through the same penetration point 32 as the catheter 920 for positioning in the subcutaneous layer 34 along the underside of the skin 30. As such, one or more of the slotted circumferential rings 930 can secure the catheter 920 in the operative position relative to the penetration point 32 without necessarily requiring adhesive tapes bonded to the skin. Each of the slotted circumferential rings 930 inserted through the skin penetration point 32 can flexibly adjust in a first direction so that the outer edge segments of the respective slotted ring 930 is shifted toward the circumferential wall of the catheter 920 (in a proximal direction toward the proximal connector hub 915). After insertion of the respective slotted ring 930 through the skin penetration point 32 and into the subcutaneous layer 34, the respective slotted ring 930 can be biased so that the outer edge segments extend generally radially outward from the circumferential wall of the catheter 920. In doing so, the respective slotted ring 930 can operate as a subcutaneous anchor that engages the underside of the skin 30, the fatty tissues in the subcutaneous layer 34, or both so as to resist withdrawal of the intravenous cannula device 505 from the skin penetration point 32. Thus, the intravenous cannula device 905 can be anchored in the operative position relative to the penetration point 32 so that the distal tip of the flexible catheter 920 resides in the targeted vessel 40 while the proximal connector hub 915 resides external to the skin 30.

Referring to FIG. 9B, during removal of the intravenous cannula device 905, each of the slotted circumferential rings 930 passing through the skin penetration point 32 can flexibly adjust in a second direction so that the outer edge segments of the respective slotted ring 930 are shifted toward the circumferential wall of the catheter 920 (in a distal direction away the proximal connector hub 915). Thus, the respective slotted ring 930 withdrawing through the skin penetration point 32 can be configured to prolapse in response to a removal force 940 applied to the intravenous cannula device 905 during withdrawal of the intravenous cannula device 905 from the skin penetration point 32. Any of the slotted circumferential rings 930 that are withdrawn through the skin penetration point 32 or are otherwise positioned external to the skin 30 can return to its non-prolapsed condition in which the slotted circumferential ring 930 is biased to extend generally radially outward from the circumferential wall of the catheter 920.

Figure 10A:
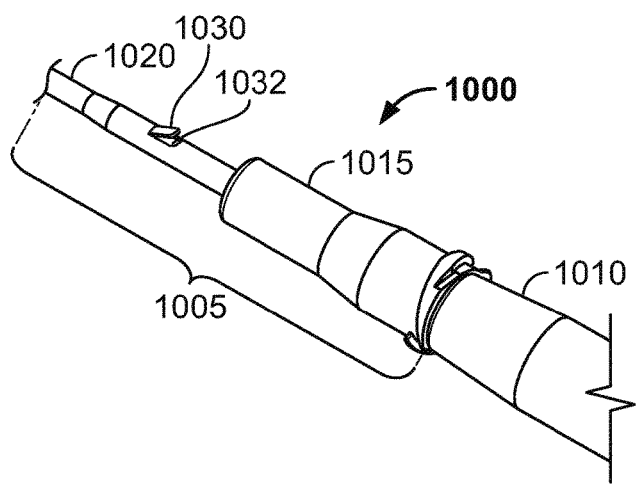
FIGS. 10A and 10B are perspective and side views of an intravenous cannula system having a subcutaneous anchor including an anchor flap, in accordance with some alternative embodiments.
Figure 10B:
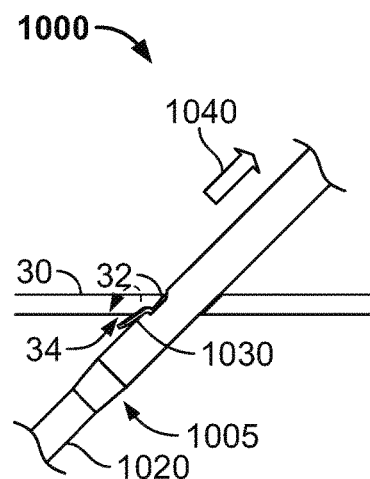

Referring now to FIGS. 10A-10B, some alternative embodiments of a medical system 1000 may include a subcutaneous anchor 1030 having a different configuration, for example, in the shape of an anchor flap. In this embodiment, the medical system 1000 can be similar to the medical system 100 of FIGS. 1-3. For example, the medical system 1000 includes an intravenous cannula device 1005 and an inserter tool 1010 that is detachably coupled to the intravenous cannula device 1005. The intravenous cannula device 1005 can include a distal section having a flexible catheter 1020 and a proximal connector hub 1015 configured to releasably connect with an external fluid line. In this embodiment, the anchor flap 1030 is integrally formed as a unitary structure with the side wall of the flexible catheter 1020, and the anchor flap 1030 is positioned along a central region of the intravenous cannula device 1005 (e.g., proximal to a distal tip of the catheter 1020 and distal to the proximal connector hub 1015).

Each recessed tab 1030 can include a corresponding cavity 1032 that is shaped to receive the anchor flap 1030 during insertion through the skin penetration point 32. In this embodiment, the anchor flap 1030 includes a generally flat shape that extends transversely from the longitudinal axis of the catheter 1020. The anchor flap 1030 can be directed to penetrate through the same penetration point 32 as the catheter 1020 for positioning in the subcutaneous layer 34 along the underside of the skin 30. As such, the anchor flap 1030 can secure the catheter 1020 in the operative position relative to the penetration point 32 without necessarily requiring adhesive tapes bonded to the skin.

In some embodiments, the anchor flap 1030 can be integrally formed with the flexible catheter 1020 such that the anchor flap 1030 and the catheter 1020 share a common flexible polymer material. Accordingly, during insertion through the skin penetration point, the anchor flap 1030 can flexibly adjust in a first direction (toward the proximal connector hub 1015) so that the anchor flap 1030 nests within its corresponding cavity 1032. After insertion of the anchor flap 1030 through the skin penetration point 32 and into the subcutaneous layer 34, the anchor flap 1030 can be biased to extend outwardly from the circumferential wall of the catheter 1020. In doing so, the anchor flap 1030 can operate as subcutaneous anchors that engages the underside of the skin 30, the fatty tissues in the subcutaneous layer 34, or both so as to resist withdrawal of the intravenous cannula device 1005 from the skin penetration point 32.

Referring to FIG. 10B, during removal of the intravenous cannula device 1005, the anchor flap 1030 can flexibly adjust in a second direction to prolapse (in a distal direction away the proximal connector hub 1015). Thus, the anchor flap 1030 can be configured to prolapse in response to a removal force 1040 applied to the intravenous cannula device 1005 during withdrawal of the intravenous cannula device 1005 from the skin penetration point 32. Optionally, the anchor flap 1030 can include a second cavity (not shown) positioned distal of the anchor flap 1030 so as to receive at least a portion of the anchor flap 1030 during removal through the skin penetration point 32.

Figure 11A:
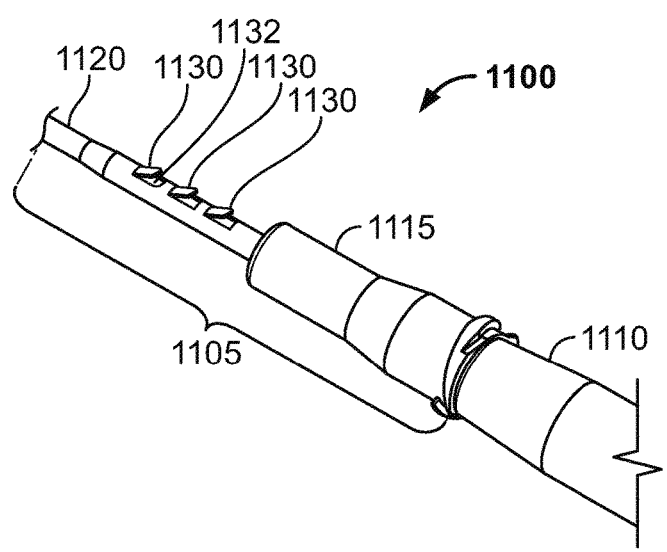
FIGS. 11A and 11B are perspective and side views of an intravenous cannula system having subcutaneous anchors including multiple anchor flaps, in accordance with some alternative embodiments.
Figure 11B:
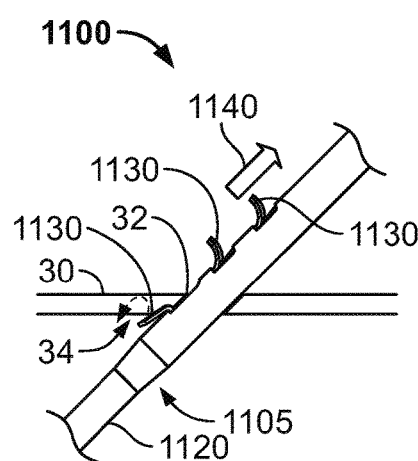

Referring now to FIGS. 11A-11B, some alternative embodiments of a medical system 1100 may include an intravenous cannula device 1105 that is similar to the device 1005 illustrated in FIGS. 10A-10B, except that intravenous cannula device 1105 is equipped with multiple anchor flaps 1130 that are operable to provide subcutaneous anchoring. Similar to previously described embodiments herein, the medical system 1100 includes the intravenous cannula device 1105 and an inserter tool 1110 that is detachably coupled to the intravenous cannula device 1105. The intravenous cannula device 1105 can include a distal section having a flexible catheter 1120 and a proximal connector hub 1115 configured to releasably connect with an external fluid line. In this embodiment, each of the anchor flaps 1130 is integrally formed as a unitary structure with the side wall of the flexible catheter 1120, and the anchor flaps 1130 are positioned in series along a central region of the intravenous cannula device 1105 (e.g., proximal to a distal tip of the catheter 1120 and distal to the proximal connector hub 1115).

Similar to the embodiments previously described in connection with FIGS. 10A-10B, one or more of the anchor flaps 1130 can be directed to penetrate through the same penetration point 32 as the catheter 1120 for positioning in the subcutaneous layer 34 along the underside of the skin 30.

In doing so, one or more of the anchor flaps 1130 can secure the catheter 1120 in the operative position relative to the penetration point 32 without necessarily requiring adhesive tapes bonded to the skin. Each of the anchor flaps 1130 inserted through the skin penetration point 32 can flexibly adjust in a first direction (toward the proximal connector hub 1115) so that each of the respective flaps 1130 nests within its corresponding cavity 1132. After insertion of the respective anchor flap 1130 through the skin penetration point 32 and into the subcutaneous layer 34, the respective anchor flap 1130 can be biased to extend outwardly from the circumferential wall of the catheter 1120 (similar to the previous embodiments described in connection with FIGS. 6A-6B). In doing so, the respective anchor flap 1130 can operate as a subcutaneous anchor that engages the underside of the skin 30, the fatty tissues in the subcutaneous layer 34, or both so as to resist withdrawal of the intravenous cannula device 1105 from the skin penetration point 32.

Referring to FIG. 11B, during removal of the intravenous cannula device 1105, each of the anchor flaps 1130 passing through the skin penetration point 32 can flexibly adjust in a second direction to bend or prolapse (in a distal direction away the proximal connector hub 1115). Thus, the respective anchor flap 1130 withdrawing through the skin penetration point 32 can be configured to prolapse in response to a removal force 1140 applied to the intravenous cannula device 1105 during withdrawal of the intravenous cannula device 1105 from the skin penetration point 32. Any of the anchor flaps 1130 that are withdrawn through the skin penetration point 32 or are otherwise positioned external to the skin 30 can return to their non-prolapsed condition in which the anchor flaps 1130 are biased to extend transversely to the longitudinal axis of the catheter 1120. Optionally, each of the anchor flaps 1130 can include a second cavity (not shown) positioned distal of the respective anchor flap 1130 so as to receive at least a portion of the respective anchor flap 1130 during removal through the skin penetration point 32.

Figure 12A:
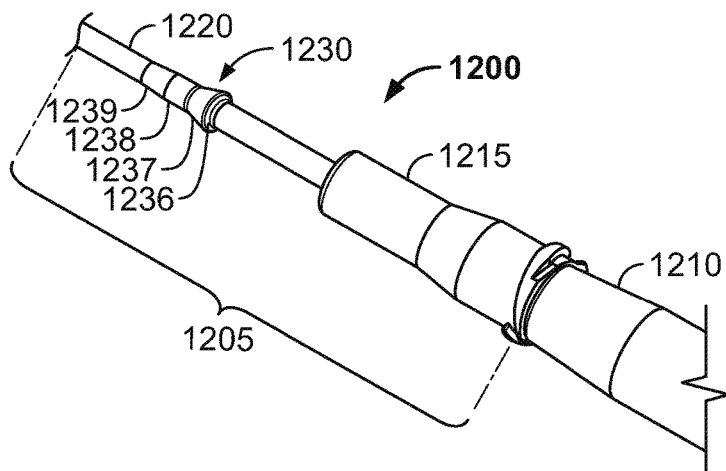
FIGS. 12A and 12B are perspective and side views of an intravenous cannula system having a subcutaneous anchor including a tapered circumferential ring, in accordance with some alternative embodiments.
Figure 12B:
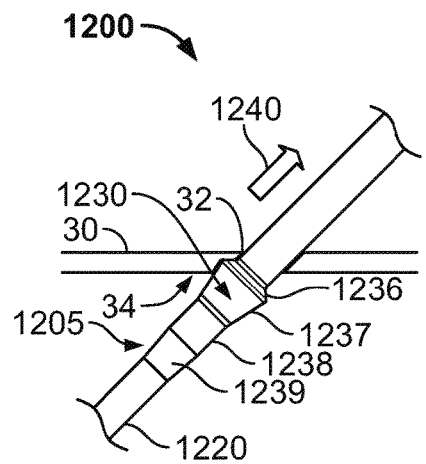

Referring now to FIGS. 12A-12B, some alternative embodiments of a medical system 1200 may include a subcutaneous anchor 1230 having a different configuration, for example, in the shape of a tapered circumferential ring. Similar to previously described embodiments, the medical system 1200 can include an intravenous cannula device 1205 and an inserter tool 1210 that is detachably coupled to the intravenous cannula device 1205. The intravenous cannula device 1205 can include a distal section having a flexible catheter 1220 and a proximal connector hub 1215 configured to releasably connect with an external fluid line. In this embodiment, the tapered circumferential ring 1230 is integrally formed as a unitary structure with the side wall of the flexible catheter 1220, and the tapered circumferential ring 1230 is positioned along a central region of the intravenous cannula device 1205 (e.g., proximal to a distal tip of the catheter 1220 and distal to the proximal connector hub 1215).

The tapered circumferential ring 1230 can be directed to penetrate through the same penetration point 32 as the catheter 1220 for positioning in the subcutaneous layer 34 along the underside of the skin 30. As such, the tapered circumferential ring 1230 can secure the catheter 1220 in the operative position relative to the penetration point 32 without necessarily requiring adhesive tapes bonded to the skin. In some embodiments, the tapered circumferential ring 1230 may be asymmetrical along its axis. For example, the tapered circumferential ring 1230 may include a proximal tapered face 1236 at a proximal end nearest to the proximal connector hub 1215. The proximal tapered face 1236 may expand distally from an initial diameter (e.g., substantially equal to the diameter of the catheter 1220) at the proximal end of the tapered circumferential ring 1230 to a maximum diameter of the tapered circumferential ring 1230 along the distal border of the proximal tapered face 1236. The diameter of the tapered circumferential ring 1230 then reduces along one or more distal tapered sections 1237, 1238, and 1239. In general, the slope of the proximal tapered face 1236 may be substantially greater (e.g., steeper) than the aggregate slopes of the tapered sections 1237, 1238, and 1239. In some embodiments, such longitudinally asymmetrical configurations may reduce the relative insertion resistance while also increasing the relative withdrawal resistance of the tapered circumferential ring 1230 through the penetration point 32.

After insertion of the tapered circumferential ring 1230 through the skin penetration point 32 and into the subcutaneous layer 34, the tapered circumferential ring 1230 can operate as a subcutaneous anchor that engages the underside of the skin 30, the fatty tissues in the subcutaneous layer 34, or both so as to resist withdrawal of the intravenous cannula device 1205 from the skin penetration point 32. During removal of the intravenous cannula device 1205 (FIG. 12B), the tapered circumferential rings 1230 withdrawing through the skin penetration point 32 can be configured to pass through the skin penetration point 32 in an atraumatic manner when a removal force 1240 is applied to the intravenous cannula device 1205.

Figure 13A:
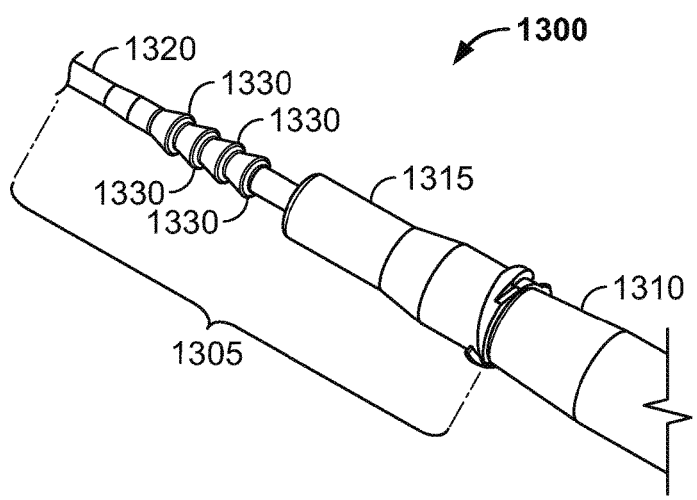
FIGS. 13A and 13B are perspective and side views of an intravenous cannula system having subcutaneous anchors including multiple tapered circumferential rings, in accordance with some alternative embodiments.
Figure 13B:
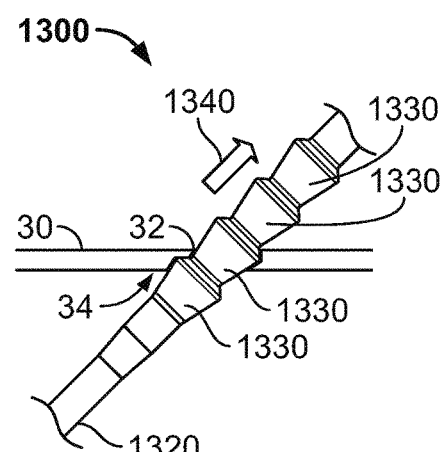

Referring now to FIGS. 13A-13B, some alternative embodiments of a medical system 1300 may include an intravenous cannula device 1305 that is similar to the device 1205 illustrated in FIGS. 12A-12B, except that intravenous cannula device 1305 is equipped with multiple tapered circumferential rings 1330 positioned in a series. Similar to previously described embodiments herein, the medical system 1300 includes the intravenous cannula device 1305 and an inserter tool 1310 that is detachably coupled to the intravenous cannula device 1305. The intravenous cannula device 1305 can include a distal section having a flexible catheter 1320 and a proximal connector hub 1315 configured to releasably connect with an external fluid line. In this embodiment, each of the tapered circumferential rings 1330 is integrally formed as a unitary structure with the side wall of the flexible catheter 1320, and the tapered circumferential rings 1330 are positioned in series along a central region of the intravenous cannula device 1305 (e.g., proximal to a distal tip of the catheter 1320 and distal to the proximal connector hub 1315).

Similar to the embodiments previously described in connection with FIGS. 12A-12B, one or more of the tapered circumferential rings 1330 can be directed to penetrate through the same penetration point 32 as the catheter 1320 for positioning in the subcutaneous layer 34 along the underside of the skin 30. In doing so, one or more of the tapered circumferential rings 1330 can secure the catheter 1320 in the operative position relative to the penetration point 32 without necessarily requiring adhesive tapes bonded to the skin. Each of the tapered circumferential rings 1330 can include a proximal tapered face that engages the underside of the skin 30, the fatty tissues in the subcutaneous layer 34, or both so as to resist withdrawal of the intravenous cannula device 1305 from the skin penetration point 32. During removal of the intravenous cannula device 1305 (FIG. 13B), the respective tapered circumferential rings 1330 withdrawing through the skin penetration point 32 can be configured to pass through the skin penetration point 32 in an atraumatic manner when a removal force 1340 is applied to the intravenous cannula device 1305.

Figure 14A:
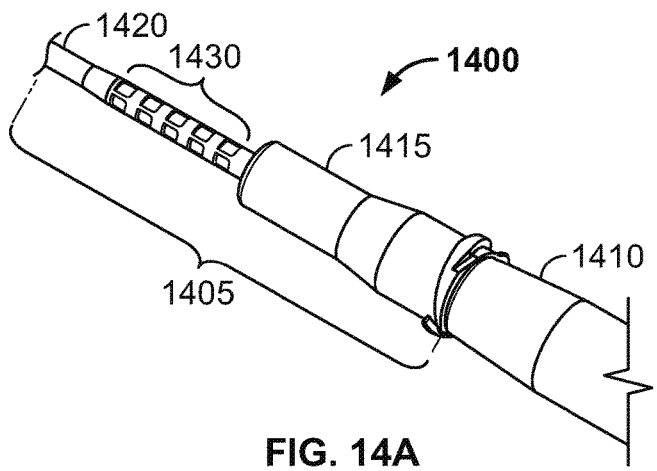
FIGS. 14A and 14B are perspective and side views of an intravenous cannula system having subcutaneous anchors including textured cutouts, in accordance with some alternative embodiments.
Figure 14B:
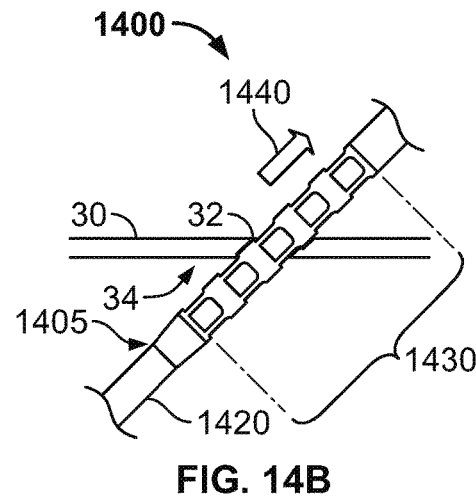

Referring now to FIGS. 14A-14B, some alternative embodiments of a medical system 1400 may include an intravenous cannula device 1405 that is similar to the device 105 illustrated in FIGS. 1-3, except that intravenous cannula device 1405 is equipped with multiple textured cutouts 1430. Similar to previously described embodiments herein, the medical system 1400 includes the intravenous cannula device 1405 and an inserter tool 1410 that is detachably coupled to the intravenous cannula device 1405. The intravenous cannula device 1405 can include a distal section having a flexible catheter 1420 and a proximal connector hub 1415 configured to releasably connect with an external fluid line. In this embodiment, the textured cutouts 1430 include sidewalls integrally formed as a unitary structure with the side wall of the flexible catheter 1320, and the textured cutouts 1430 are positioned in series along a central region of the intravenous cannula device 1405 (e.g., proximal to a distal tip of the catheter 1420 and distal to the proximal connector hub 1415). In the depicted embodiment, the textured cutouts 1430 may be formed in the sidewall of the flexible catheter 1420 as a set of scalloped cavities configured to anchor within the subcutaneous layer. Some or all of the textured cutouts 1430 can be directed to penetrate through the same penetration point 32 as the catheter 1420 for positioning in the subcutaneous layer 34 along the underside of the skin 30. In doing so, one or more of the textured cutouts 1430 can secure the catheter 1420 in the operative position relative to the penetration point 32 without necessarily requiring adhesive tapes bonded to the skin. Each of the textured cutouts 1430 can include a least one cavity sidewall that engages the underside of the skin 30, the fatty tissues in the subcutaneous layer 34, or both so as to resist withdrawal of the intravenous cannula device 1405 from the skin penetration point 32. During removal of the intravenous cannula device 1405 (FIG. 14B), the respective textured cutouts 1430 withdrawing through the skin penetration point 32 can be configured to pass through the skin penetration point 32 in an atraumatic manner when a removal force 1440 is applied to the intravenous cannula device 1405.

Figure 15A:
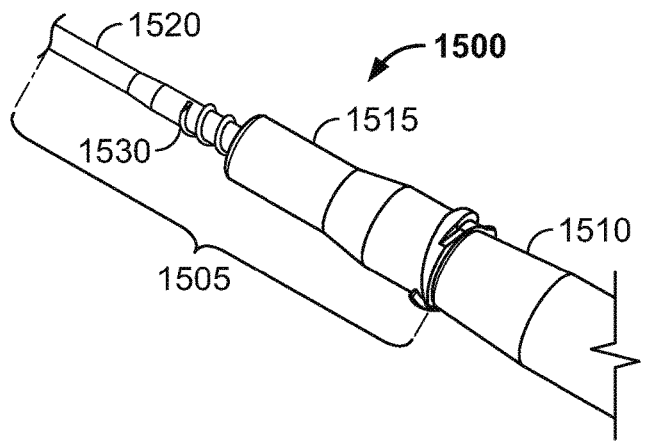
FIGS. 15A and 15B are perspective and side views of an intravenous cannula system having a subcutaneous threaded anchor, in accordance with some alternative embodiments.
Figure 15B:
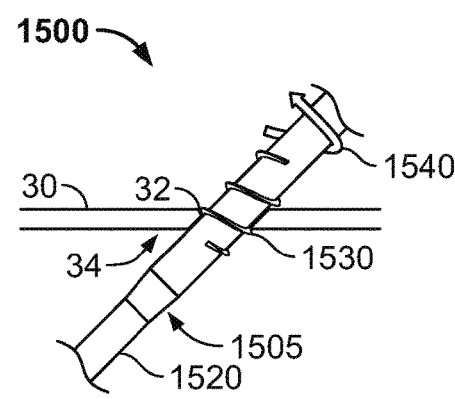

Referring now to FIGS. 15A-15B, some alternative embodiments of a medical system 1500 may include an intravenous cannula device 1505 that is similar to the device 105 illustrated in FIGS. 1-3, except that intravenous cannula device 1505 is equipped with a threaded anchor 1530. Similar to previously described embodiments herein, the medical system 1500 includes the intravenous cannula device 1505 and an inserter tool 1510 that is detachably coupled to the intravenous cannula device 1505. The intravenous cannula device 1505 can include a distal section having a flexible catheter 1520 and a proximal connector hub 1515 configured to releasably connect with an external fluid line. In this embodiment, the threaded anchor 1530 include at least one thread pattern formed as a unitary structure with the side wall of the flexible catheter 1520, and the threaded anchor 1530 is positioned along a central region of the intravenous cannula device 1505 (e.g., proximal to a distal tip of the catheter 1520 and distal to the proximal connector hub 1515). In the depicted embodiment, the threaded anchor 1530 may be spiral around the side wall of the flexible catheter 1520 so that the thread is configured to anchor within the subcutaneous layer. The threaded anchor 1530 can be directed to penetrate through the same penetration point 32 as the catheter 1520 for positioning in the subcutaneous layer 34 along the underside of the skin 30. For example, during insertion of the intravenous cannula device 1505, the user can twist the inserter tool 1510 to "screw" the anchor thread through the skin penetration point 32. In doing so, the threaded anchor 1530 can secure the catheter 1520 in the operative position relative to the penetration point 32 without necessarily requiring adhesive tapes bonded to the skin. The threaded anchor 1530 can include a least one thread wall surface that engages the underside of the skin 30, the fatty tissues in the subcutaneous layer 34, or both so as to resist withdrawal of the intravenous cannula device 1505 from the skin penetration point 32. During removal of the intravenous cannula device 1505 (FIG. 15B), the threaded anchor can be removed through the skin penetration point 32 by twisting the proximal connector hub 1515 with a removing force 1540 so as to "unscrew" the threaded anchor 1530 out of the skin penetration point 32 in an atraumatic manner.

Figure 16A:
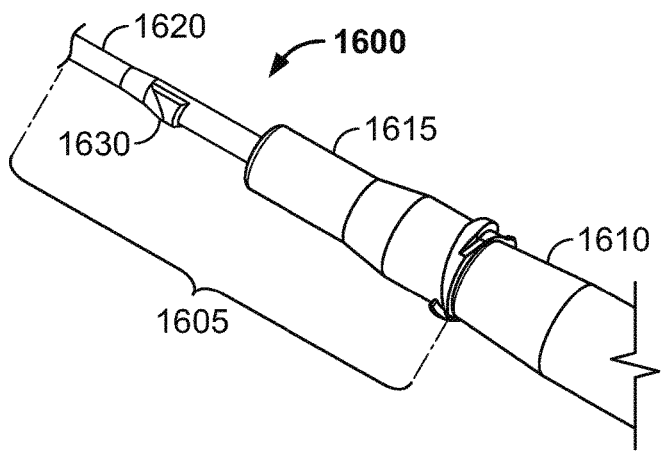
FIGS. 16A and 16B are perspective and side views of an intravenous cannula system having a subcutaneous anchor including a wedge, in accordance with some alternative embodiments.
Figure 16B:
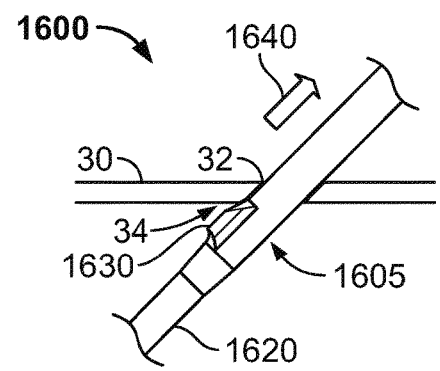

Referring now to FIGS. 16A-16B, some alternative embodiments of a medical system 1600 may include an intravenous cannula device 1605 that is similar to the device 105 illustrated in FIGS. 1-3, except that intravenous cannula device 1605 is equipped with a wedge anchor 1630. Similar to previously described embodiments herein, the medical system 1600 includes the intravenous cannula device 1605 and an inserter tool 1610 that is detachably coupled to the intravenous cannula device 1605. The intravenous cannula device 1605 can include a distal section having a flexible catheter 1620 and a proximal connector hub 1615 configured to releasably connect with an external fluid line. The wedge anchor 1630 can be positioned along a central region of the intravenous cannula device 1605 (e.g., proximal to a distal tip of the catheter 1620 and distal to the proximal connector hub 1615). In the depicted embodiment, the wedge anchor 1630 is asymmetrical in shape. For example, in a cross sectional view taken parallel to the longitudinal axis of the catheter 1620, the wedge anchor 1630 may appear generally trapezoidal in shape, in which the upper and lower sides of the trapezoid are substantially parallel to the axis of the catheter 1620, and a proximal side has a steeper angle than a distal side. In some embodiments, this longitudinally asymmetrical configuration can reduce the relative insertion resistance while also increasing the relative extraction resistance of the wedge anchor 1630 through the penetration point 32.

The wedge anchor 1630 can be directed to penetrate through the same penetration point 32 as the catheter 1620 for positioning in the subcutaneous layer 34 along the underside of the skin 30. In doing so, the wedge anchor 1630 can secure the catheter 1620 in the operative position relative to the penetration point 32 without necessarily requiring adhesive tapes bonded to the skin. The wedge anchor 1630 can include a least one sidewall (e.g., the aforementioned steep proximal side wall) that engages the underside of the skin 30, the fatty tissues in the subcutaneous layer 34, or both so as to resist withdrawal of the intravenous cannula device 1605 from the skin penetration point 32. During removal of the intravenous cannula device 1605 (FIG. 16B), the user can lightly move the intravenous cannula device 1605 in a back-and-forth lateral movement while applying a longitudinal withdrawal force 1640 so that the wedge anchor 1630 passes through the skin penetration point 32 in an atraumatic manner.

A number of embodiments of the invention have been described. Nevertheless, it will be understood that various modifications may be made without departing from the scope of the invention. Accordingly, other embodiments are within the scope of the following claims.

What is claimed is:

1. A medical system for anchoring an intravenous cannula device under a skin layer, comprising:
   an intravenous cannula device including a flexible catheter having a distal opening configured to provide fluid communication into a targeted vessel, a proximal connector hub, and a tissue anchor device, the tissue anchor device being positioned along the flexible catheter between the distal tip opening of the flexible catheter and the proximal connector hub, the flexible catheter including a lumen and extending distally of the proximal connector hub to the distal opening, and the proximal connector hub including a thread pattern configured to releasably connect with an external fluid line; and
   an inserter tool removably coupled to the intravenous cannula device so as to insert the flexible catheter of the intravenous cannula device through a skin penetration point and into the targeted vessel, the inserter tool including a handle and an insertion needle extending distally from the handle, the insertion needle being slidably engaged with the lumen of the flexible catheter of the intravenous cannula device, wherein the inserter tool is removable from the intravenous cannula device when the insertion needle is proximally withdrawn from the lumen of the flexible catheter,
   wherein the tissue anchor device is configured to anchor the outer wall under the skin layer when the flexible catheter of the intravenous cannula device is inserted through the skin penetration point and into the targeted vessel.

2. The system of claim 1, wherein the tissue anchor device comprises one or more flexible circumferential rings integrally formed as a unitary structure with the outer wall of the flexible catheter.

3. The system of claim 2, wherein each of the one or more flexible circumferential rings are configured to prolapse and extend toward a distal end of the flexible catheter during removal through the skin penetration point.

4. The system of claim 1, wherein the tissue anchor device comprises one or more pairs of recessed tabs integrally formed as a unitary structure with the outer wall of the flexible catheter, wherein each respective recessed tab includes a corresponding cavity to receive the recessed tab during insertion through the skin penetration point.

5. The system of claim 4, wherein each of the one or more pairs of recessed tabs are configured to prolapse such that free ends of the recessed tabs extend toward a distal end of the flexible catheter during removal through the skin penetration point.

6. The system of claim 1, wherein the tissue anchor device comprises one or more slotted circumferential rings integrally formed as a unitary structure with the outer wall of the flexible catheter.

7. The system of claim 6, wherein each of the one or more slotted circumferential rings are configured to prolapse and extend toward a distal end of the flexible catheter during removal through the skin penetration point.

8. The system of claim 1, wherein the tissue anchor device comprises one or more anchor flaps integrally formed as a unitary structure with the outer wall of the flexible catheter, wherein each of the one or more anchor flaps comprises a generally straight body that extends transversely to a longitudinal axis of the flexible catheter.

9. The system of claim 1, wherein the tissue anchor device comprises one or more tapered circumferential rings integrally formed as a unitary structure with the outer wall of the flexible catheter, wherein each of the tapered circumferential rings have an asymmetric shape in which a proximal face is steeper than a distal tapered face.

10. The system of claim 1, wherein the tissue anchor device comprises a set of textured cutouts integrally formed as a unitary structure with the outer wall of the flexible catheter, wherein each of the textured cutouts are defined by cavity walls formed in the outer wall of the flexible catheter.

11. The system of claim 1, wherein the tissue anchor device comprises a threaded anchor integrally formed as a unitary structure with the outer wall of the flexible catheter, wherein the threaded anchor comprises a raised thread pattern helically extending around the outer wall of the flexible catheter.

12. The system of claim 1, wherein the tissue anchor device comprises a wedge anchor integrally formed as a unitary structure with the outer wall of the flexible catheter, wherein the wedge anchor comprises an asymmetric shape having a proximal face and a distal face, the proximal face defines an incline relative to the outer wall of the flexible catheter that is greater than an incline defined by the distal face.

13. The system of claim 1, wherein the proximal connector hub is fixedly attached to a proximal end of the flexible catheter.

14. The system of claim 1, wherein the proximal connector hub has a longitudinal length extending from a proximal end of the proximal connector hub to a distal end of the proximal connector hub, wherein the longitudinal length of the proximal connector hub is greater than a maximum outer diameter of the proximal connector hub.

15. The system of claim 14, wherein the tissue anchor device has a maximum lateral width that is less than a minimum outer diameter of the proximal connector hub.

16. The system of claim 1, wherein the tissue anchor device includes at least one surface to engage tissue in a subcutaneous region along an underside of a skin layer when the flexible catheter of the intravenous device is inserted through the skin penetration point and into a targeted vessel.

17. The system of claim 1, wherein the tissue anchor device includes at least one surface to engage an underside of the skin layer when the flexible catheter of the intravenous cannula device is inserted through the skin penetration point and into a targeted vessel.

18. A method of using an intravenous cannula device, comprising:
   inserting a needle portion of an inserter tool through a skin penetration point and into a targeted vessel, wherein an intravenous cannula device is removably coupled to the inserter tool such that a flexible catheter of the intravenous cannula device is advanced through the skin penetration point and into the targeted vessel while a tissue anchor device integrally formed as a unitary structure with an outer wall of the flexible catheter is positioned under a skin layer;
   removing the inserter tool from the intravenous cannula device such that the needle portion of the inserter tool is slidably withdrawn from a lumen of the flexible catheter while a distal opening of the flexible catheter remains in the targeted vessel to provide fluid communication with a targeted vessel and the tissue anchor device remains under the skin layer;
   threadably engaging an external fluid line to a proximal connector hub of the intravenous cannula device while the flexible catheter remains in the targeted vessel and the tissue anchor device remains under the skin layer, wherein the tissue anchor device is positioned between a distal tip of the flexible catheter and the proximal connector hub; and infusing a fluid from the proximal connector hub through the lumen of the flexible catheter and into the targeted vessel.

19. The method of claim 18, wherein the tissue anchor device includes at least one surface to engage tissue in the subcutaneous region proximate to the skin penetration point.

20. The method claim 19, further comprising applying a withdrawal force to the proximal connector hub of the intravenous cannula device so as to withdrawal the tissue anchor device through the skin penetration point.

\* \* \* \* \*